US010080892B2

(12) United States Patent
Southwell et al.

(10) Patent No.: US 10,080,892 B2
(45) Date of Patent: *Sep. 25, 2018

(54) TRANSCUTANEOUS STIMULATION METHOD AND SYSTEM

(71) Applicant: Murdoch Childrens Research Institute, Parkville, Victoria (AU)

(72) Inventors: Bridget Rae Southwell, Gordon (AU); John Medwyn Hutson, East Malvern (AU); Andre Yi Feng Tan, Mulgrave (AU)

(73) Assignee: Murdoch Childrens Research Institute, Parkville (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/634,961

(22) Filed: Jun. 27, 2017

(65) Prior Publication Data

US 2017/0348526 A1 Dec. 7, 2017

Related U.S. Application Data

(62) Division of application No. 13/824,314, filed as application No. PCT/AU2012/000212 on Mar. 2, 2012, now Pat. No. 9,789,308.

(Continued)

(51) Int. Cl.
*A61N 1/36* (2006.01)
*A61N 1/04* (2006.01)

(52) U.S. Cl.
CPC ....... *A61N 1/36007* (2013.01); *A61N 1/0452* (2013.01); *A61N 1/0456* (2013.01);
(Continued)

(58) Field of Classification Search
None
See application file for complete search history.

(56) References Cited

U.S. PATENT DOCUMENTS 4,381,012 A 4/1983 Russek
4,690,144 A 9/1987 Rise et al.
(Continued)

FOREIGN PATENT DOCUMENTS

GB 960682 6/1964
JP 02-206475 8/1990
(Continued)

OTHER PUBLICATIONS

Chase et al., 2005, Pilot Study Using Transcutaneous Electrical Stimulation (Interferential Current) to Treat Chronic Treatment-Resistant Constipation and Soiling in Children, Journal of Gastroenterology and Hepatology, 20:1054-1061.
(Continued)

*Primary Examiner* — Ankit D Tejani
(74) *Attorney, Agent, or Firm* — Knobbe Martens Olson & Bear LLP

(57) ABSTRACT

A method of treating a waste evacuation dysfunction comprising administering transcutaneous electrical stimulation (TES) to at least one lower pelvic and/or sacral region for a specific treatment regimen. Also disclosed is a system for configuring a stimulation device to deliver transcutaneous electrical stimulation (TES) the system comprising: a computing device storing or having access to a plurality of TES settings and comprising a user interface to enable authorized selection of at least one of the TES settings for provision of TES by the stimulation device according to the at least one selected TES setting and the stimulation device communicatively coupled to the computing device to receive and store the selected at least one TES setting the stimulation device being of a size to be readily carried on a body and configured to selectively provide current to external electrode according to the one TES setting.

20 Claims, 10 Drawing Sheets

Related U.S. Application Data

(60) Provisional application No. 61/448,378, filed on Mar. 2, 2011.

(52) U.S. Cl.
CPC ......... *A61N 1/0476* (2013.01); *A61N 1/0484* (2013.01); *A61N 1/0492* (2013.01); *A61N 1/36014* (2013.01)

(56) References Cited

U.S. PATENT DOCUMENTS

| | | | |
|---|---|---|---|
| 5,562,717 | A | 10/1996 | Tippey et al. |
| 5,871,534 | A | 2/1999 | Messick et al. |
| 6,445,955 | B1 | 9/2002 | Michelson et al. |
| 6,728,577 | B2 | 4/2004 | Minogue et al. |
| 8,000,792 | B1 | 8/2011 | Dechev et al. |
| 8,019,426 | B2 | 9/2011 | Moore et al. |
| 2004/0030267 | A1 | 2/2004 | Orten |
| 2005/0055054 | A1 | 3/2005 | Yu |
| 2005/0075678 | A1 | 4/2005 | Faul |
| 2005/0278001 | A1 | 12/2005 | Qin et al. |
| 2006/0009815 | A1 | 1/2006 | Boveja |
| 2006/0089683 | A1 | 4/2006 | Hagglof et al. |
| 2006/0184211 | A1 | 8/2006 | Gaunt et al. |
| 2006/0195153 | A1 | 8/2006 | Diubaldi et al. |
| 2007/0055337 | A1 | 3/2007 | Tanrisever |
| 2007/0150034 | A1 | 6/2007 | Rooney |
| 2007/0156183 | A1 | 7/2007 | Rhodes |
| 2007/0255085 | A1 | 11/2007 | Kishawi et al. |
| 2008/0077192 | A1 | 3/2008 | Harry |
| 2008/0147143 | A1 | 6/2008 | Popovic et al. |
| 2008/0208287 | A1 | 8/2008 | Palermo |
| 2008/0249591 | A1 | 10/2008 | Gaw et al. |
| 2009/0048642 | A1 | 2/2009 | Goroszeniuk |
| 2009/0157149 | A1 | 6/2009 | Wahlgren et al. |
| 2009/0182393 | A1 | 7/2009 | Bachinski |
| 2010/0049027 | A1 | 2/2010 | Teschner et al. |
| 2010/0152817 | A1 | 6/2010 | Gillbe |
| 2011/0015689 | A1* | 1/2011 | Rhodes ................. A61N 1/323 607/10 |
| 2011/0230701 | A1 | 9/2011 | Simon |
| 2011/0295339 | A1 | 12/2011 | Carroll |
| 2012/0029591 | A1 | 2/2012 | Simon |
| 2012/0116477 | A1 | 5/2012 | Crowe et al. |
| 2012/0221973 | A1 | 8/2012 | Southwell et al. |
| 2013/0123568 | A1 | 5/2013 | Hamilton et al. |
| 2014/0148871 | A1 | 5/2014 | Southwell et al. |
| 2016/0235981 | A1 | 8/2016 | Southwell et al. |
| 2016/0250463 | A1 | 9/2016 | Southwell et al. |
| 2017/0182318 | A1 | 6/2017 | Fisher et al. |

FOREIGN PATENT DOCUMENTS

| | | |
|---|---|---|
| JP | 08-501946 | 3/1996 |
| JP | 10-179768 | 7/1998 |
| JP | 2001-170190 | 6/2001 |
| JP | 2001-238967 | 9/2001 |
| JP | 2007-037853 | 2/2007 |
| JP | 2008-307382 | 12/2008 |
| JP | 2009-136585 | 6/2009 |
| WO | WO 08/137162 | 11/2008 |
| WO | WO 11/026166 | 3/2011 |
| WO | WO 12/116407 | 9/2012 |
| WO | WO 15/051405 | 4/2015 |
| WO | WO 15/051406 | 4/2015 |

OTHER PUBLICATIONS

Clarke et al., 2009, Decreased colonic transit time after transcutaneous interferential electrical stimulation in children with slow transit constipation, Journal of Pediatric Surgery, 44(2):408-412.
Clarke et al., 2009, Improvement of quality of life in children with slow transit constipation after treatment with transcutaneous electrical stimulation. J Pediatr Surg, 44: 1268-1273.
Clarke et al., 2012, Transabdominal electrical stimulation increases colonic propagating pressure waves in paediatric slow transit constipation. J Pediatr Surg. 47(12):2279-2284.
De Paepe et al., 2002, The role of pelvic-floor therapy in the treatment of lower urinary tract dysfunctions in children, Scand J Urol Nephrol. 36(4):260-267 (abstract).
Ismail et al., 2009, Daily transabdominal electrical stimulation at home increased defecation in children with slow-transit, J Pediatr Surg, 44: 2388-2392.
Kajbafzadeh et al., 2012, Transcutaneous interferential electrical stimulation for management of neurogenic bowel dysfunction in children with myelomeningocele. Int J Colorectal Dis, 27:453-458.
Koklu et al., May 2010, Clinical trial: interferential electric stimulation in functional dyspepsia patents—a prospective randomized study, Aliment Pharmacol Ther, 31:961-968.
Leong et al., 2001, Long-term effects of transabdominal electrical stimulation in treating children with slow-transit constipation, Journal of Pediatric Surgery, 46:2309-2312.
Queralto et al., Interferential Therapy: a new treatment for slow transit constipation. A pilot study in adults. Colorectal Dis 2012: 15: e35-e39.
Sikiru et al., Nov.-Dec. 2008, Transcutaneous electrical nerve stimulation (TENS) in the symptomatic management of chronic prostatitis/chronic pelvic pain syndrome: a placebo-control randomized trial, International Braz J Urol., 34(6):708-713.
Southwell, 2013, Medical devices to deliver transcutaneous electrical stimulation using interferential current to treat constipation, Expert Rev. Med. Devices, 19(6):701-704.
Southwell, B. Treatment of slow transit constipation in children. Fifth European Paediatric Motility Meeting, J Pediatr Gastroenterol Nutr 2011; 53: Suppl 2 s 551-3.
Stillman et al., 2006, Strengthening of the pelvic floor muscles using transcutaneous magnetic nerve stimulation: a review of the literature. Australian and New Zeland Continence Journal. 12(2):31-40.
Veiga ML, Lordêlo P, Farias T, Barroso U Jr. Evaluation of constipation after parasacral transcutaneous electrical nerve stimulation in children with lower urinary tract dysfunction—a pilot study. J Pediatr Urol. 2013; 9(5):622-6.
Vitton et al., 2009, Transcutaneous Posterior Tibial Nerve Stimulation for Fecal Incontinence in Inflammatory Bowel Disease Patients: A Therapeutic Option?, Inflammatory Bowel Diseases, 15(3):402-405.
Yik et al., 2011, Slow-transit constipation with concurrent upper gastrointestinal dysmotility and its response to transcutaneous electrical stimulation. J Pediatr Surg Int, 27(7):705-711.
Yik et al., 2012, Home transcutaneous electrical stimulation to treat children with slow-transit constipation, Journal of Pediatric Surgery, 47:1285-1290.
Yik et al., 2012, The impact of transcutaneous electrical stimulation therapy on appendicostomy operation rates for children with chronic constipation—a single—institution experience, Journal of Pediatr Surg, 47: 1421-1426.
Yik et al., 2013, Home Transcutaneous Electrical Stimulation (TES) Therapy to Treat Children with Anorectal Retention (AR): A Pilot Study. Gastroenterology, 144(5):S364.
Yik et al., 2013, Treatment Resistant Slow-Transit Constipation (STC) in Children Can Be Improved With Home-Based Transcutaneous Electrical Stimulation. Gastroenterology, 144(5):S399.
Office action dated Jun. 14,2016 in Russian office action No. 2013144203.
Chase et al., Abstract for oral presentation on "Daily transcutaneous electrical stimulation (using interferential current) at home increased defecation in children with slow transit constipation: a pilot study," Neurogastroenterology and Motility 2009, Joint International Meeting, Chicago Aug. 27-30, Abstract published on Jul. 1, 2009, p. 3.
Ismail et al., Daily transcutaneous electrical stimulation at home increased defecation in children with slow transit constipation: a pilot study, 42nd Annual Meeting of Pacific Association of Pediatric Surgeons, May 10-14, 2009, Hong Kong, abstract, pp. 216-217.
Ismail et al., J Pediatr Surg website screen capture showing article preview with publication date of Dec. 2009 for article Daily transabdominal electrical stimulation at home increased defecation

(56) References Cited

OTHER PUBLICATIONS in children with slow-transit, J Pediatr Surg, 44: 2388-2392 (retrieved on Jul. 28, 2017, from: http://www.jpedsurg.org/article/50022-3468(09)00640-X/pdf).

Ismail et al., PubMed website screen capture showing article preview with publication date of Dec. 2009 for article "Daily transabdominal electrical stimulation at home increased defecation in children with slow-transit," J Pediatr Surg, 44: 2388-2392 (retrieved on Jul. 28, 2017, from: http://www.sciencedirect.com/science/article/pii/S002234680900640X).

Ismail et al., ScienceDirect website screen capture showing article preview with publication date of Dec. 2009 for article "Daily transabdominal electrical stimulation at home increased defecation in children with slow-transit," J Pediatr Surg, 44: 2388-2392 (retrieved on Jul. 28, 2017, from: http://www.sciencedirect.com/science/article/pii/S002234680900640X).

\* cited by examiner

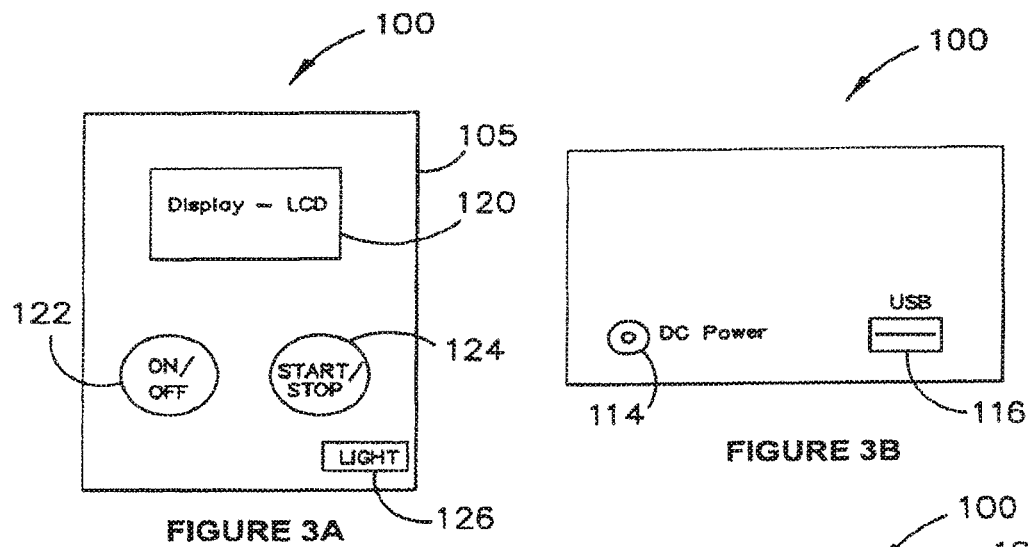
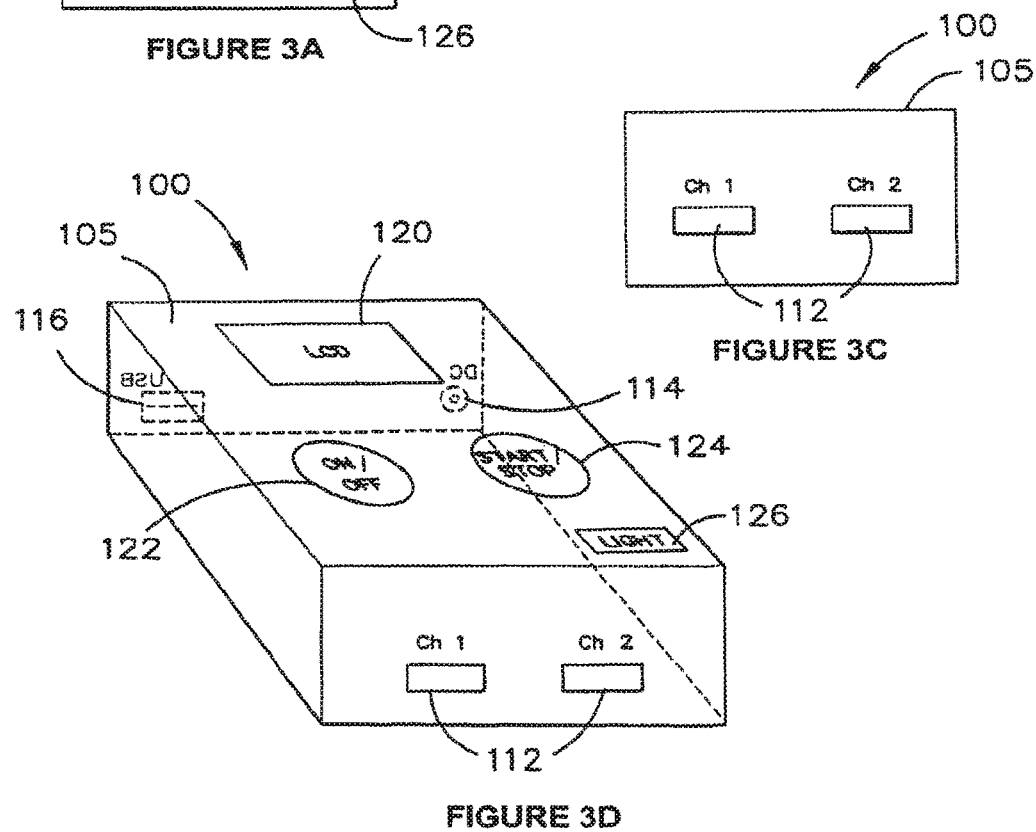

TRANSCUTANEOUS STIMULATION METHOD AND SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application is a divisional of U.S. application Ser. No. 13/824,314, filed May 28, 2013, entitled "Transcutaneous Stimulation Method and System," which is a U.S. National Phase Application of PCT International Application number PCT/AU2012/000212, filed Mar. 2, 2012, entitled "Transcutaneous Stimulation Method and System" and designating the United States of America and published in the English language, which claims the benefit of priority of U.S. provisional application No. 61/448,378, filed Mar. 2, 2011, entitled "Transcutaneous Stimulation Method and System," the entire disclosure of each of which is incorporated herein by reference for all purposes.

FIELD

Described embodiments relate generally to methods and systems for transcutaneous stimulation. More particularly, methods, systems, devices and apparatus for transcutaneous stimulation in one or more of the lumbar, abdominal, lower pelvic and sacral regions are described to treat one or more dysfunctions associated with a body's ability to evacuate waste.

BACKGROUND

Reference to any prior art in this specification is not, and should not be taken as, an acknowledgment or any form of suggestion that this prior art forms part of the common general knowledge in any country.

Reference in this specification to any prior publication (or information derived from it), or to any matter which is known, is not, and should not be taken as, an acknowledgment or admission or any form of suggestion that that prior publication (or information derived from it) or known matter forms part of the common general knowledge in the field of endeavour to which this specification relates.

Bibliographic details of the publications referred to by author in this specification are collected alphabetically at the end of the description.

Waste elimination dysfunction can take many forms. For example, urinary incontinence, intestinal incontinence or constipation can occur.

Treatment systems exist for treating constipation by providing electrical stimulus via subcutaneously implanted electrodes positioned around the lower bowel. Electrical stimulation provided using such electrodes can be used to sequentially activate muscle fibres around the bowel to force a peristaltic action to occur. However, such treatment systems are undesirably invasive. Further, while such systems may have an immediate effect in assisting to evacuate the bowel, they do not necessarily address the cause of the constipation. Importantly, this effect has not been described as long lasting or having an effect beyond the immediate time of electrical stimulation.

Intractable constipation and soiling are extremely common in the community, in both the young and old, and available treatments are generally uncomfortable, can cause social distress for sufferers and are a significant drain on the health care system. Individuals that suffer from constipation and soiling who are young or old may also have psychological issues. In addition, constipation may be a side effect of some kinds of medication, such as opiates. Most laxative therapies are designed to either soften the stool or stimulate the bowel by chemicals in the lumen. Patients with chronic constipation or intractable constipation may have failed other treatment methods including pharmaceutical treatment. Patients on therapies for other diseases in which constipation is a side effect of the medication may not be able to be co-administered pharmaceutical treatments for constipation. Non-invasive, non-drug-based treatment methodologies may be desired in such cases.

Sometimes constipation may be unrelated to diet or medications, and can be due to poor motility in the whole colon (Benninga et al, *J Pediatr Gastroenterol Nutr.*, 23:241-51, 1996; Hutson et al, *J Pediatr Surg.*, 31:580-583, 1996). A newly identified disorder, which is known as slow-transit constipation (STC), is not uncommon amongst children who fail standard medical therapy, and such children often have signs of colonic dysfunction even at birth. (Shin et al, *J Pediatr Surg.*, 37:1762-1765, 2002).

Previous electrical stimulation involved non-daily stimulation (i.e. 12 sessions in 4 week period) of short periods (i.e. 20 min of treatment) using transcutaneous devices that have been developed for physiotherapy treatment of muscular injuries (Clarke et al, *J. Pediatr. Surg.*, 44:408-412, 2009.)

It is desired to address or ameliorate one or more disadvantages or shortcomings associated with existing treatment systems, methods or regimes, or to at least provide a useful alternative thereto.

SUMMARY

Non-invasive electrical stimulation apparatus, devices, methods and systems are described herein to be used specifically for the treatment of constipation and improved treatment regimens. This treatment may have long term benefits in some patients with continued improvement after the period of treatment by the non-invasive electrical stimulation.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Some embodiments relate generally to treatment regimes for transcutaneous stimulation. More particularly, methods, devices, apparatus and systems are provided for treating constipation or another waste evacuation dysfunction by the administration of transcutaneous electrical stimulation to at least one lumbar and/or abdominal region for a period of time on a daily basis or greater than 12 sessions in a 4 week period. The electrical stimulation may alternatively or additionally be administered to a lower pelvic and/or sacral region. Reference to "greater than 12 sessions" includes from about 12 to about 100 sessions such as about 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 sessions, for example, or even more.

In some embodiments, the treatment may involve a single treatment session each day or multiple (e.g. 2 or 3) treatment sessions per day. The treatment sessions may be for periods of between about 10 and about 90 minutes or from about 20 and about 60 minutes. Other time periods include about 11, 12, 13, 14, 15, 16, 17, 18, 19, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 61, 62, 63, 64, 65, 66, 67, 68, 69, 70, 71, 72, 73, 74, 75, 76, 77, 78, 79, 80, 81, 82, 83, 84, 85, 86, 87, 88 and 89 minutes, for example.

In some embodiments, the daily (or greater than 12 sessions in a 4 week period) electrical stimulation regime may be performed as part of a longer-term treatment plan, in which the stimulation is performed daily or greater than 12 sessions in a 4 week period for between about 2 weeks and 2 to 3 months. This includes periods of about 3, 4, 5, 6, 7, 8, 9, 10, 11, 12 and 13 weeks, for example. The regime may also involve repeating the longer-term treatment within periods of about 4 months to two years. Such longer-term periods include about 4, 5, 6, 7, 8, 9, 10, 11, 12, 13, 14, 15, 16, 17, 18, 19, 20, 21, 22, 23 and 24 months, for example. The transcutaneous electrical treatment may provide a longer term effect of greater than 1 day, for example up to 1 month to 1 year or more. Hence, the effect of treatment lasts beyond the immediate time of electrical stimulation.

In some embodiments, where daily treatment (or greater than 12 treatment sessions in a 4 week period) is anticipated, for ease of administration, the treatment device is such that it can be used at home without the supervision of a trained professional during the daily (or greater than 12 sessions in a 4 week period) treatment regimen.

The stimulation may be performed using one to ten electrodes, for example, placed on the lumbar and/or lower front abdominal areas. Electrodes may be additionally or alternatively placed over the lower pelvic and/or sacral regions, including the buttocks or other tissue overlying or adjacent the ilium, to excite or modulate the nerves and other tissues around the rectum, including the recto-sigmoid colon.

In particular embodiments, an even number of electrodes are employed in a spaced pair arrangement. Alternatively, one, three, five or more electrodes may be employed. In some embodiments, the one to ten or more electrodes may be fixed in an apparatus such as a belt. The fixed positioning of the electrodes in a device such as a belt may aid in the positioning of the electrodes to the lumbar and/or lower front abdominal areas and the spacing of the electrodes. The electrodes used to provide the electrical stimulation may be provided on a carrier that can be removably affixed, for example by adhesion, to a desired skin surface area to facilitate appropriate spacing of the electrodes from each other.

The electrodes may be coupled to and receive a stimulation current from a stimulation device having a low voltage, low current power source. The stimulation device may comprise a handheld portable device, for example, that can be operated without needing to be coupled to an external power supply. The stimulation device may be configured to be powered by a disposable and/or rechargeable battery or other small self-contained power source, for example. The power source of the stimulation device may be rechargeable, for example by coupling it via a transformer to a mains power supply. The stimulation device may be configured to prevent or minimise the current supply to the electrodes while the stimulation device is having its portable power source recharged.

The stimulation device may provide or consist of a primitive display, for example to indicate its on/off state, whether it is in use (i.e. providing stimulation signals), a display of an accrued time of use and/or a remaining time for use in a particular session. The stimulation device may also be configured to prevent electrical stimulation being provided for more than a predetermined total amount of time for a day or 24 hour period or for more than a predetermined amount of time (e.g. 60, 70, 80 or 90 minutes) in any one usage session. Alternatively or in addition, the device may be configured to restrict the total amount of electrical energy delivered to the stimulation electrodes over a usage session or a particular period of time.

The stimulation device may be free of external manually operable mechanisms but for an on/off button or switch and a stop/start button or switch. In some alternative embodiments, the stimulation device may have external manually operable mechanisms, for example to interface with a device display, but may be free of any manually operable mechanisms to provide input to the stimulation device that would alter device settings or parameters according to which the electrical stimulation signals are provided.

In some embodiments, the stimulation device is configured to only operate according to a single set of operating parameters at a given time. In some embodiments, this single set of operating parameters may only be replaced with another single set of operating parameters using an electronic configuration interface separate from but communicably coupleable to the stimulation device. For example, the stimulation device may be provided with a default set of operating parameters by a manufacturer of the device, and this set of parameters may be subsequently modified by a therapist using software authorized to reconfigure the settings of the stimulation device via a wired or wireless connection. In other embodiments, the stimulation device may be configurable (e.g. by a trained professional using authorised software) with multiple stored sets of stimulation settings for separate use by multiple users. Thus, the user interface of the stimulation device may be configured to be quite simple and to disallow user modification of the settings, in order to facilitate ease and appropriateness of use of the device. However, in alternative embodiments, the stimulation device may have greater user interface functionality and may allow for one of two, three, four or more stimulation settings to be selected by a user.

In some embodiments, the stimulation device may be pre-configured or configurable to provide output signals to stimulation electrodes having an approximately sinusoidal form, with an approximately 4 kilohertz carrier frequency, roughly 80 to 150 hertz modulated frequency and a current intensity of around 5 to around 33 milliamps Such stimulation signals may be applied to two or four or more electrodes, for example including two electrodes spaced across the lower front abdominal area and two electrodes spaced across the lumbar area, applying interferential current stimulation from left front to right back and/or right front to left back.

In some embodiments, the stimulation frequency may be selected or configured to take account of the Body Mass Index (BMI) of the patient, which can be different for a child versus an adult, and also whether the patient is of normal weight, overweight, obese or underweight.

Some embodiments relate to a system for configuring a stimulation device to deliver transcutaneous electrical stimulation (TES), the system comprising:
    a computing device storing or having access to a plurality of TES settings and comprising a user interface to enable authorised selection of one of the TES settings for provision of TES by the stimulation device according to the one setting; and the stimulation device communicatively coupled to the computing device to receive and store the selected one TES setting, the stimulation device being of a size to be readily carried on a body and configured to selectively provide current to external electrodes according to the one TES setting.

In some embodiments, the stimulation device may receive and store multiple selected TES settings for delivering TES to multiple users.

BRIEF DESCRIPTION OF THE DRAWINGS

Embodiments will now be described in further detail, by way of example, with reference to the accompanying drawings, in which:

FIGS. 3A, 3B, 3C and 3D are schematic diagrams of an example stimulation device in different views;

DETAILED DESCRIPTION

Figure 1:
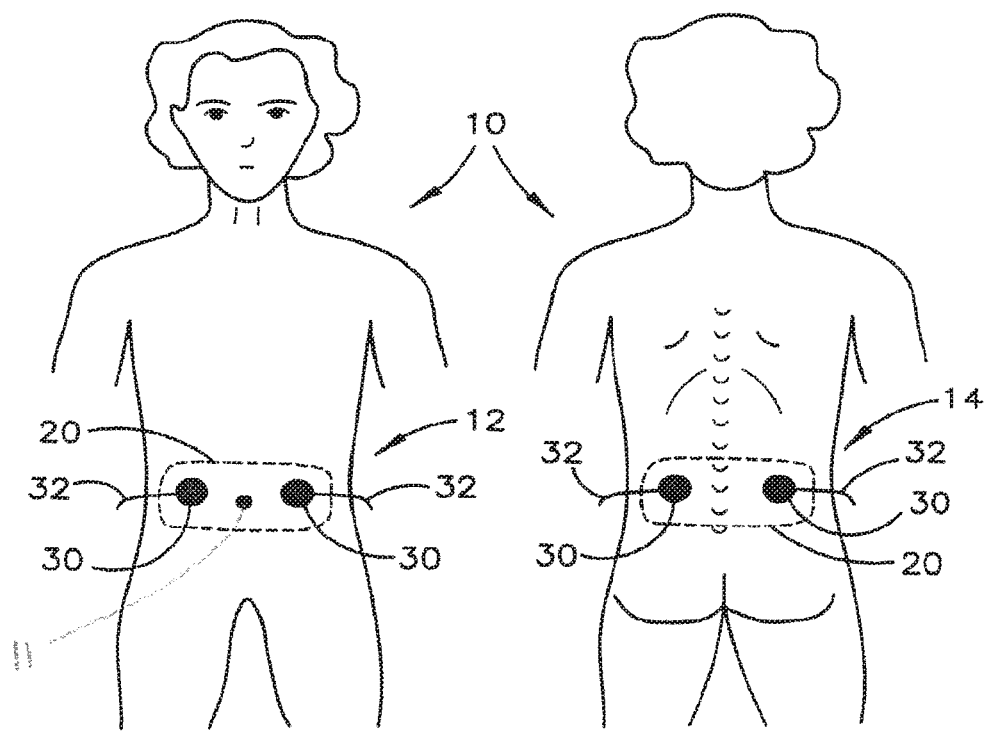
FIG. 1 is a schematic diagram illustrating use of electrical stimulation to treat intestinal dysfunction in a child.

Embodiments herein relate generally to methods, systems, devices and treatment regimes for treating or enabling the treatment of a waste elimination dysfunction, such as, for example and without limitation, constipation, ileus, urinary incontinence or intestinal incontinence. Such embodiments generally involve the application of transcutaneous electrical stimulation (TES) to a front or back (lumbar) abdominal region for at least one treatment session per day over consecutive days of a treatment period of at least one week. TES may alternatively or additionally be applied to lower pelvic and/or sacral regions including the buttocks, to excite or modulate the nerves and other tissues around the rectum, including the recto-sigmoid colon.

The term "waste evacuation dysfunction" or "waste elimination dysfunction" used herein is intended to include dysfunction associated with a body's gastrointestinal and urinary waste processing and/or elimination functions, whether or not the processing actually immediately results in evacuation or elimination of the waste from the body. For example, ileus or slow transit of waste through parts of the intestinal tract to the rectum are considered to be waste evacuation dysfunctions in this sense because they affect the body's process of eliminating that waste from the body, even though the ileus or slow transit may be accurately described as a dysfunction preceding the actual elimination of that waste.

The treatment session may be performed multiple times per day or just once and may be performed for a time between about 10 and about 90 minutes for each session. In some embodiments, the treatment session may be between about 20 minutes and about 60 minutes, preferably closer to 60 minutes, such as 25, 30, 35, 40, 45, 50, 55, 65 or 70 minutes or other times in between.

In some embodiments, daily treatments are anticipated of greater than 12 sessions in a 4 week period (i.e. three sessions per week). For ease of administration, the treatment device is such that it can be used at home without the supervision of a trained healthcare professional during the daily (or greater than 3 sessions a week) treatment regimen.

The treatment term of at least one week may be, for example, between about 2 weeks and about 3 months. In some embodiments, the treatment term may be between about 1 month and about 2 months.

The treatment term may be repeated over an extended term of from about 4 months to about 2 years or possibly more, in order to have the treatment suitably program, teach or train the various muscles and/or nerves responsible for proper function of the affected organs or tissues. Thus, the treatment period may be repeated multiple times over the longer term, with the degree of repetition depending on physiological response to one or more initial treatment terms.

The treatment may have an effect beyond the immediate time of electrical stimulation which may last 1 day, for example up to 1 week, to 1 month to one year or more beyond the last time of electrical stimulation.

Figure 2:
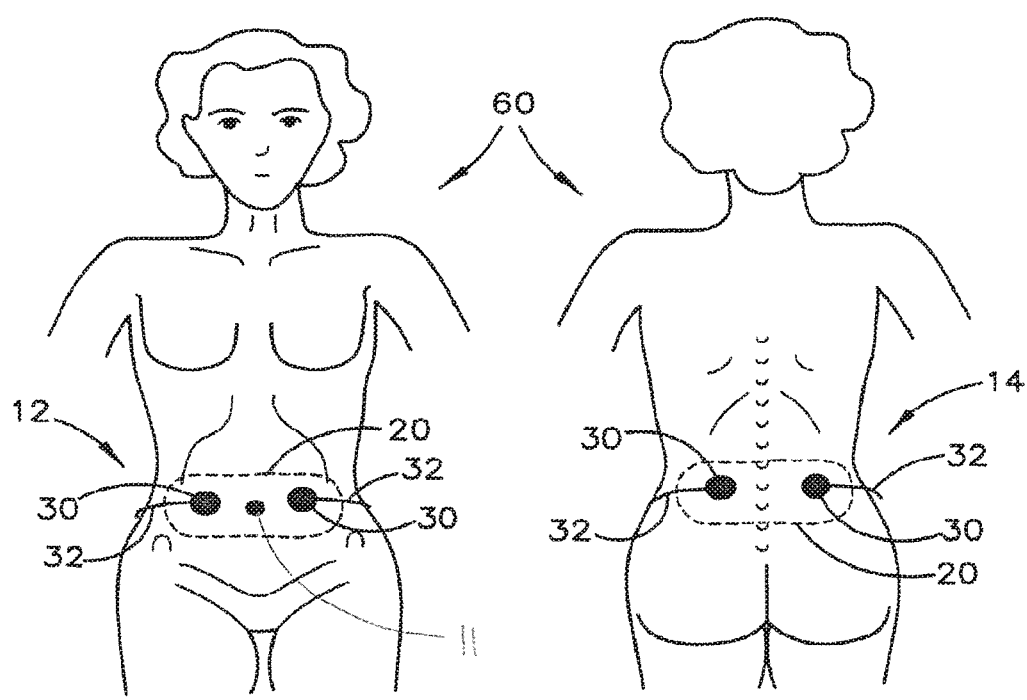
FIG. 2 is a schematic diagram illustrating use of electrical stimulation to treat intestinal dysfunction in an adult.

Generally, as illustrated in FIGS. 1 and 2 in relation to a child 10 or adult 60, the electrical stimulation may be provided to electrodes 30 positioned over a front abdomen region 12 (on either side of the umbilicus 11) and/or on a back (lumbar) abdominal region 14. The electrodes 30 receive electrical stimulation signals via conductors 32 to which they are coupled and convey these to the skin surface of the child 10 or adult 60 to which they are affixed or otherwise conductively positioned against. A suitable conductive gel may be used to increase conductivity of the electrical signals from electrodes 30 into the body via the skin.

In some embodiments, four surface electrodes 30 may be used, two electrodes 30 being positioned one to either side of the umbilicus 11 on the anterior abdominal wall beneath the costal margin, and two electrodes 30 being positioned on the para-spinal area of T9-10 to L2. Positioning of the electrodes 30, whether four or more than four electrodes 30 are used, is intended to stimulate the proximal colon (including at least part of the ascending colon and the transverse colon) and at least an upper part of the descending colon, which generally correlates to the abdominal vicinity of the umbilicus 11. Positioning of the electrodes 30 is not made to particularly affect the sigmoid colon or distal parts of the descending colon or rectum. Thus, although the positioning of the electrodes 30 is applied to provide stimulation to parts of the large bowel closer to the costal margin, not necessarily all of the large bowel is to be stimulated in this way.

Lateral spacing of the electrode positions from the umbilicus 11 may be in the vicinity of 1, 2, 5 or 8 to 20 cm, for example, thereby providing a lateral separation between the electrodes 30 of about 2, 4, 10 or 15 to 40 cm. Other lateral spacings within such ranges may be employed, as appropriate. The electrodes 30 may be positioned approximately level with the umbilicus 11, although some small variation of locations, for example slightly closer to or further from the costal margin, may be employed. The electrodes 30 positioned in the para-spinal area may be located substantially directly across the abdomen from the frontal electrodes 30. In some embodiments, the electrodes 30 may be slightly offset from each other vertically or laterally across the pelvis and/or abdomen.

Electrodes 30 may be provided on a carrier 20 that comprises a flexible substrate conveniently positioning the electrodes 30 a fixed distance apart from each other to assist in proper positioning of the electrodes in one or more regions 12, 14. The flexible substrate 20 may comprise adhesive substances on one or more portions thereof in order to facilitate removable application of electrodes 30 to the skin and retention of the electrodes 30 in a specific selected location. Each carrier 20 may comprise 1, 2, 3, 4, 5, 6, 7, 8, 9, 10 or more electrodes 30 in specific spaced relation. Once the electrodes 30 are appropriately positioned, either with or without the aid of a carrier 20, electrode conductor leads 32 are used to couple the conductors 30 to respective channels 139a, 139b (FIG. 4) of a stimulation device 100.

Figure 4:
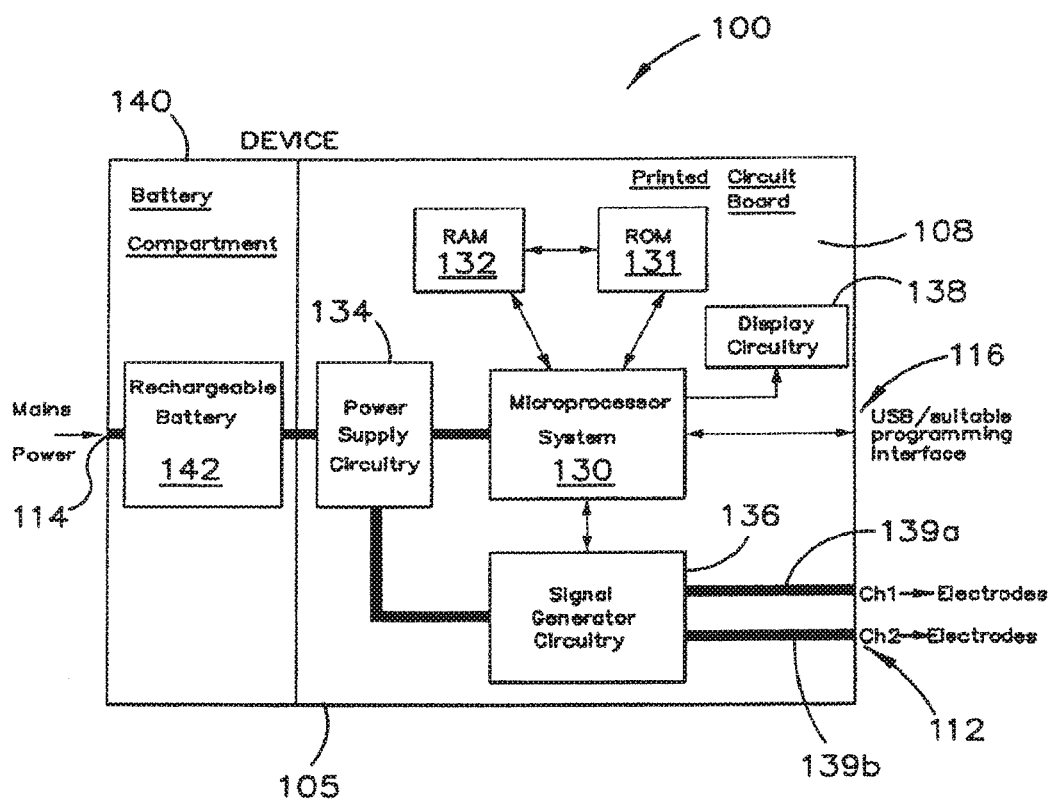
FIG. 4 is a block diagram of the stimulation device.

A stimulation device 100 and its components and features are described in further detail below, with reference to FIGS. 3A, 3B, 3C, 3D and 4. FIG. 3A is a schematic plan view of the device 100. FIG. 3B is one end view of the device 100. FIG. 3C is an opposed end view of the device 100. FIG. 3D is a schematic perspective view of the device 100. FIG. 4 is a block diagram of the device 100, showing components and circuitry housed within a casing 105 of device 100. Stimulation device 100 is designed to be simple, portable and light, so that it can be worn by a user, possibly within a carrier belt, while it provides the stimulation signals to the electrodes 30 as the user performs normal activities.

The portable stimulator device 100 is designed to provide therapeutic electrical stimulation for individuals suffering dysfunction. Device 100 delivers a specified electrical signal to the patient through a set of electrodes that are placed on the skin surface of the abdomen, lower back, lower pelvis and/or sacral region. The device is designed to be as simple as possible, optionally in combination with a belt to assist electrode positioning (FIG. 10), so that those with relatively low technological sophistication, including some children and the elderly, may operate the device without clinical supervision (e.g. at home) and with minimal complication. It has been found that devices employing too much user interface sophistication are liable to be misused, with the result being that the patient may experience pain from improper treatment or may not receive the intended therapeutic benefit of the treatment. Some embodiments of device 100 thus provide a simplified on/off type of user interface, leaving any selection or reconfiguration of stimulation settings to be performed by a trained clinician or therapist using external software.

Device 100 may be provided with an accompanying software package for use by a patient or the patient's carer on a separate computer system 605 (FIG. 6) to facilitate user education and instruction. Additionally, separate software may be provided for use by a clinician to allow the clinician to set or modify settings or functions of device 100 to further benefit patients.

The device 100 is configured to allow its internal software (firmware) to be easily updated. Should more effective treatment settings be determined, the device 100 can be updated through a firmware update so that patients can have access to different treatment regimes or settings.

The device 100 is small enough for a small child to carry, and variations of the design may feature child-friendly shapes and colours through changeable faceplates and covers, and also larger, Braille-studded or other tactile buttons and/or displays for vision-impaired or geriatric users.

Measures to provide device safety may include short-circuit protections, isolated charging circuits to prevent mains power being delivered to a user in the event of device malfunction and conditional operation failsafe mechanisms (i.e. the device cannot be operated if electrodes 30 and/or electrode leads 32 are not connected or not correctly connected).

The device 100 may feature one or more of:

1. Two independent electrical channels 139a, 139b, each of which is capable of providing a specified current, voltage and waveform characteristic via electrode leads 32 to electrodes 30.

2. A display 120 including a liquid crystal display (LCD) and/or an LED-based display or other form of display such as light 126, responsive to signals received at display circuitry 138 from microprocessor 130 to display some or all of the following information:
   a. ON/OFF status of the device 100.
   b. The remaining battery life of the device 100.
   c. START/STOP status of the electrical stimulation.
   d. A timer to indicate elapsed and/or remaining time of stimulation for a treatment session.

3. An ON/OFF switch or button 122 to turn on or off the device 100.

4. A START/STOP switch or button 124 to turn on or off the electrical stimulation signals.

Device 100 may comprise various communication and power supply inputs, including (but not limited to):
   a. Stimulator electrode sockets 112—these allow the electrode leads and wires to plug into the device. As a failsafe, the device 100 may be configured to not be operable unless the electrode leads and electrodes are correctly attached and connected. In some embodiments, more than two (e.g. four) sockets 112 may be provided and/or more than two (e.g. four) interferential current channels may be provided in order to be able to deliver interferential TES to multiple frontal and posterior electrode pairs.
   b. DC power supply socket 114 to supply the device and internal battery 142 with power. The power may be converted from mains power (110V/240 V 60/50 Hz) to a suitable DC voltage via a switched-mode power supply (SMPS) or other suitable electrical power converter.
   c. A computer interface port 116 (Universal Serial Bus, or other industry standard computer interface, wired or wireless) to allow authorized users to add, modify or change the function of the device, based on the level of authority.
   d. A reset button (not shown) that cannot be easily accessed, but be accessible, for example through battery compartment 140, should a device reset be required.

e. An in-built speaker (not shown) to provide audible messages, beeps, alerts or other signals to vision-impaired users and younger users.

Device 100 may comprise a rigid casing 105 to house the electronics (e.g. on PCB 108) and may comprise environmental sealing to industry standards (i.e. rubber gaskets on exposed connectors, rubber sealing within the device to stop liquids and other foreign material from breaching the device casing).

Device 100 may further comprise one or more accelerometers to detect and record movement and/or orientation of device 100, to thereby infer one or more states or situations of use. Additionally, device 100 may have means for sensing and recording temperature, for example via the electrodes 30, in order to infer additional information concerning use of device 100. This patient usage information can then be used to assess patient compliance with the treatment regime.

Device 100 may, in some embodiments, comprise selection means, such as a button or buttons, dial, touch-pad or touch-screen, in cooperation with display 120, to vary the current intensity of TES to be delivered via electrodes 30. This permissible variation may be limited to within a predetermined or pre-set range, for example. In some further embodiments, the selection means may be employed in combination with multiple personalised stimulation settings (for multiple different people) stored into the device, possibly by a clinician in consultation with the people for whom the TES is intended. This may allow a single device 100 to be used in a setting where multiple users are present, such as a nursing home or other shared accommodation or treatment facility.

The physical size or external appearance of the device 100 may vary depending on the target market. It may:
a. Be small enough to fit in a small bag that a child can easily carry, may feature various case styles and designs to give it a child-friendly appearance, and make it more appealing to young users.
b. Be large enough to be handled by geriatric users, and feature:
  i. Extra-large LCD (or other display) with larger symbols (if a display is provided).
  ii. Large buttons for easy operation.
  iii. Braille embedded on various parts of the device and tactile buttons to allow users with poor vision to operate it.
c. Feature an exterior casing/faceplate that may be changeable to modify the physical appearance of the device so that the user may customise the "look" of the device to taste (i.e. a case that looks like a rabbit for young children, a case that looks like a car for a 10-yr old male user, a doll for a 6-yr old female user). This case is completely separate from the internal case 105 that houses the device's electronics.

The device 100 may comprise a battery compartment 140 defined by casing 105 and housing a (optionally rechargeable) battery 142 that can be coupled to an external power supply via socket 114. Battery 142 supplies a DC voltage, such as 9 V, to power supply circuitry 134, which supplies power to the various electrical/electronic components of device 100.

The device 100 comprises a combination of programmable and non-programmable circuitry, digital or analog, embedded onto or coupled to at least one printed circuit board (PCB) 108. The circuitry includes, but is not limited to:

1. Signal generator circuitry 136 to produce the electrical waveforms provided to channels 139*a*, 139*b*. As a failsafe, signal generator circuitry 136 may be current-limited to prevent oversupply of current.

2. An on-board microprocessor system 130, which may comprise a suitable microcontroller, an Application-Specific Integrated Circuit (ASIC) and/or Field-Programmable Gate Array (FPGA). The microprocessor system 130 has access to sufficient Read-Only Memory (ROM) 131 and Random-Access Memory (RAM) 132 to facilitate device operation, communication between external devices, firmware update functions and service/maintenance functions. Device 100 operates according to control software (firmware) pre-programmed into the ROM 132 to facilitate operation and control of the device.

3. On-board load-testing circuitry (as part of, or controlled by and responsive to, microprocessor 130) to check that each and all electrodes are connected and in proper contact to an electrical load that is representative of human tissue.

4. In-built safety features to prevent or minimise unintended current being delivered to the patient. This may include (but not be limited to):
  a. Charging circuit isolation via power supply circuitry 134 to prevent provision of electrical stimulation during a battery charge operation.
  b. Failsafe measures provided by the load-testing circuitry to prevent the provision of stimulation current from the device when improper electrical connection is detected, for example where electrodes are not connected to electrode leads, when electrode leads are not connected to the device 100, or when electrodes are incorrectly attached to the device 100 or when the electrodes are not connected to a human body.
  c. Short-circuit protections to prevent or mitigate delivery of unintended current to the patient.

Figure 5:
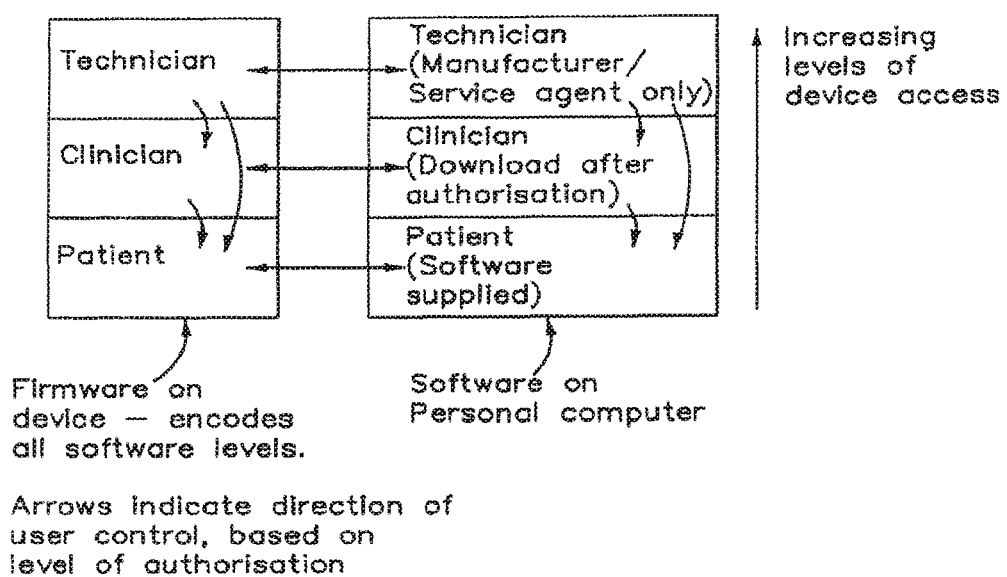
FIG. 5 is a schematic illustration of software controls applicable to use of the stimulation device.

The device software (firmware) and separate computer software (to be executed by computer system 605) may feature three modes of access by which three different classes of users can interact with it. These modes are described below and schematically illustrated in FIG. 5.

Patient Mode: The user may operate the device for therapeutic purposes, but may not modify, change or delete device functions when interacting with the physical device. An exception to this is that the user may change device function only with an authorized software (firmware) update provided by the manufacturer. This update should be sufficiently tamper-proof to prevent user errors and device corruption.

Figure 6:
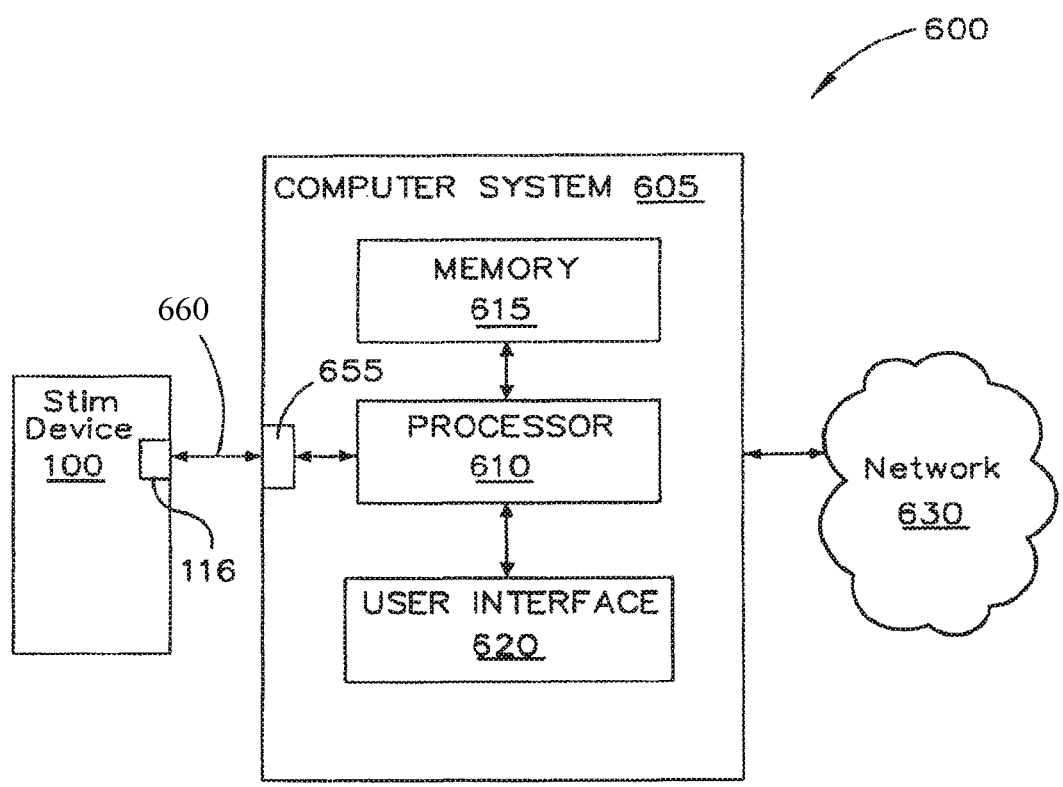
FIG. 6 is a block diagram of a system for configuration of the stimulation device.

The user may operate the personal computer software to access informational or help files to learn how to operate the device 100 or optionally to view usage statistics, for example, but may not modify, change or delete device functions when interacting with the device 100 through the personal computer interface 620 (FIG. 6). This user-focussed software may be provided when the device is purchased, either as a software CD (or other computer-readable medium) or electronic download from the manufacturer.

Clinician Mode: The clinician user may alter the device's function (in a restricted manner), for example to select different stimulation settings for device 100 to improve the therapeutic benefit of the device 100 to the patient by interacting only with the clinician-user interface module executing on computer system 605. This may include authorized firmware updates as listed in the section relating to Patient Mode.

Personal Computer software for use by the clinician may not be supplied with the device, but instead may only be obtained once a clinician has registered with the manufacturer and been certified to make limited function modifications to the device for therapeutic benefits only.

Technician/Service Mode: An authorized repair agent or manufacturer technician/engineer may access the core program of the device in order to facilitate diagnostics and repair functions. This mode allows for full/authorized modification to device function.

The software/firmware is split into two separate code modules that interact with each other:

1. Software programmed into the device 100 (firmware):
   a. The firmware may be programmed into the device 100 at the time of its manufacture. The firmware has all three levels of functionality pre-programmed, but specific functions may only be accessed by licence holders or authorized persons as specified above.
2. Software programmed for use on the computer 605:
   a. The software may only interact with its authorized level, and any levels that it is authorized to interact with. For example, the Patient Mode on the device may only interact with the Patient Mode on the computer software, and the Technician Mode may interact with both the Patient Mode and Clinician Mode.
   b. The software on the computer 605 facilitates the firmware update in an automated fashion to minimise complications in the upgrade process. This will also provide security verification so that the device cannot be tampered with through this access method.

Software and firmware updates may be provided from time to time by the manufacturer as required.

The device is intended to be operated in the following manner:

The user attaches the electrode carrier 20 and electrode pads 30 (or just the electrode pads 30 if they're not provided on a carrier 20) to the lower front abdomen and lower back as shown in FIGS. 1 (child) and 2 (adult). The electrode carrier 20 and/or electrode pads 30 may additionally or alternatively be attached in the manner shown in FIGS. 8A to 8C, 9A, 9B and 10.

The electrode leads 32 are connected to all of the electrode pads 30, and then to the correct sockets 112 on the device 100. Alternatively, leads 32 may be provided to a patient pre-connected to pads 30 and/or sockets 112.

The user then switches on the device 100 using button 122, in response to which the device 100 performs a back-end function check to ensure that all systems are normal and that electrodes 30 and electrode leads 32 are connected correctly. During this time, the LCD 120 may display a short message to the user that the device is starting up.

Once the device 100 is ready, the LCD 120 may indicate a message or signal (e.g. green LED lights up) to inform the user that stimulation is ready to start. A backlight of the START/STOP button 124 may light up and flash, and the user can then press the START/STOP button 124 to commence stimulation.

During current delivery, a counter or timer function executed by microprocessor 130 may cause display circuitry 138 coupled to display 120 to indicate the remaining stimulation time. Should the user wish to terminate current delivery, the user presses the START/STOP button 124. Pressing the ON/OFF button 122 in the ON state will also terminate current delivery and switch the device 100 off.

Once current delivery has ceased, the device 100 may indicate on the LCD 120 that stimulation for the current treatment session is complete. Should the user not press the ON/OFF button 122, the device 100 may be configured to automatically switch itself off after a manufacturer-specified time to prevent accidental operation and minimise battery consumption. The microprocessor system 130 may control device 100 to disallow further administration of stimulation for a period of several (e.g. up to 24) hours, regardless of whether device 100 is turned off. For this purpose, microprocessor 130 may comprise a suitable timer function (with possibly a long-term back-up power supply) that cannot be disrupted, even with the device 100 being switched off or the battery 142 being removed or drained. This feature may be disabled or not present in embodiments of device 100 configured for use by multiple different users.

Device 100 may, in alternative embodiments, comprise greater user interface functionality than is described above, for example in order to enable a user to select from a number of stimulation settings, including carrier frequency, modulated frequency, current intensity, duration of the treatment session, etc. However, regardless of the user interface functionality of device 100, it should be operable to provide a stimulation current of magnitude less than about 40 mA at a carrier frequency of between about 1 kHz and about 10 kHz, with a modulated frequency of about 20 to about 300 Hz.

Preferably, the device 100 is configured to provide stimulation currents having a magnitude of 33 to 40 mA or less (but more than zero) at a carrier frequency of about 4 kHz, with a modulated frequency of about 80 Hz to 150 Hz. The electrical stimulation may be provided as interferential electrical stimulation, for example from left front to right back and/or right front to left back.

In some embodiments, because the electric current is delivered transcutaneously to the individual, the amount of electrical stimulation to be delivered to an individual may vary from individual to individual based on either Body Mass Index (BMI) and/or circumference at waist and/or weight. For example, the optimal energy for electrical stimulation required for a normal weight child would be less than for an obese child. An algorithm for determining the electrical stimulation energy required, for example based on age, BMI, weight, or circumference around the waist, may be included in the device firmware, together with operating parameters to allow specific electrical stimulation parameters to be initially set by the treating clinician or other medically trained professional.

One specific dysfunction that some embodiments are considered suitable for treating is slow transit constipation (STC). However, described embodiments may be applied to treat various other waste evacuation dysfunctions, such as other types of constipation, incontinence, irritable bowel syndrome (IBS) and ileus, for example. In some embodiments, stimulation device 100 may be coupled to computer system 605, as shown in FIG. 6. In the illustrated arrangement, computer system 605 and stimulation device 100 form part of a system 600 for facilitating configuration of device 100 and/or facilitating communication between stimulation device 100 and computer system 605 or a network 630 to which computer system 605 is coupled. Computer system 605 may comprise a desktop, laptop or handheld computing device having a processor 610, memory 615 and user interface 620. Processor 610 may comprise more than one processing device and has access to memory 615 which comprises volatile and non-volatile storage for executing software functions as described herein. User interface 620 comprises normal peripheral devices and/or user interface functionality for facilitating user interaction with computer system 605 and may include suitable display-related software in addition to the normal display screen, keyboard, mouse, touch screen and/or stylus, etc.

Computer system 605 comprises an input/output port 655 for communicating via a wired or wireless connection 660 with port 116 of stimulation device 100, thus enabling processor 610 to reconfigure (to the extent permitted) or otherwise interface with stimulation device 100. Ports 116 and 655 may adopt a common configuration, for example according to the universal serial bus (USB) standard or may have a non-standard proprietary port/communication configurations. Computer system 605 may be a computer system used by a patient to interface with stimulation device 100, for example in order to communicate with (or even power up using USB power, for example) stimulation device 100.

Alternatively, computer system 605 may be a computing device used by a clinician, such as a specialist therapist, to select one or a few configuration settings stored locally on system 605 or accessible to system 605 (for example over network 630), from among multiple possible selections to be used to configure or reconfigure the stimulation settings of device 100. The software operable on system 605 in order to effect such reconfiguration of device 100 may be stored in memory 615 and executable by processor 610. Such software may be downloaded from a remote location over network 630 in response to suitable accreditation or authentication of the clinician for use of such reconfiguration software.

As a further alternative, computer system 605 may be a computer used by a technician or manufacturer to interface with device 100 as needed, for example in order to provide initial or default stimulation settings.

Figure 8:
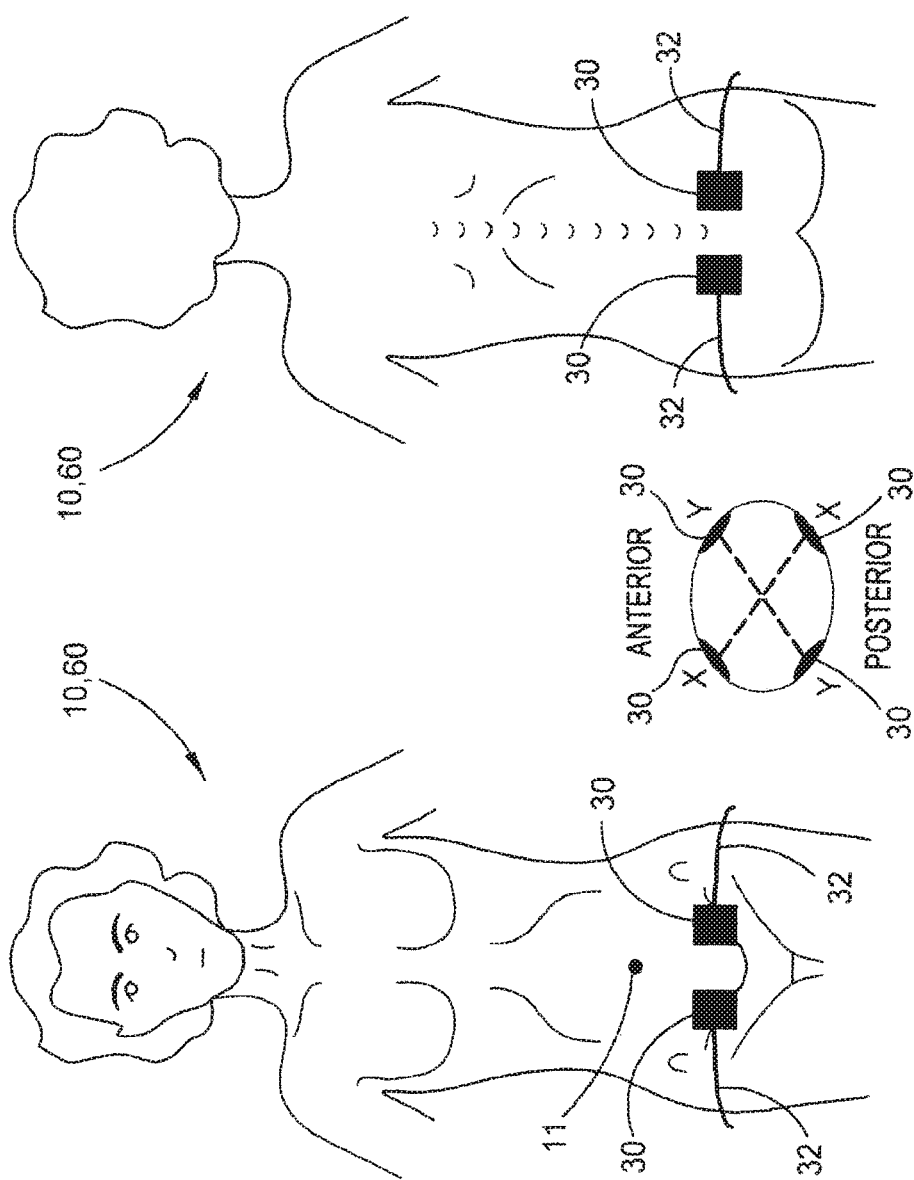
FIG. 8A is a schematic illustration showing placement of electrodes in a lower pelvic region on a person's front side.
FIG. 8B is a schematic representation of placement of electrodes in a sacral or lower lumbar region on a backside of the person.
FIG. 8C is a schematic plan view illustrating crossing interferential currents between the lower pelvic and sacral or lower lumbar region electrodes.

In some embodiments, the electrodes 30 may be positioned in regions closer to the anus, for example, in an anterior lower pelvic area and in a posterior sacral or lower lumbar region, as illustrated in FIGS. 8A and 8B. Such electrode positioning is believed to assist with treatment of anorectal retention (AR) as evidenced by the information described in Example 3 below. Other than the lower positioning of the electrodes 30, such embodiments use device 100 in combination with conductors 32 and electrodes 30 in the same way as described above.

As is illustrated in FIGS. 8A to 8C, the lower positioning of the electrodes 30 is intended to excite or modulate nerves and tissues around the recto-sigmoid colon to assist in evacuation of faecal matter accumulating in the large bowel distal of the proximal colon (i.e. through the descending colon, the sigmoid colon and the rectum). FIG. 8C illustrates schematically how the crossing interferential currents are arranged between front left and back right (X to X) and between front right and back left (Y to Y).

The anterior electrodes 30 are positioned between about 1 and about 10 cm laterally apart relative to the vertical centre line of the umbilicus 11 in a lower pelvic area not extending down to the genitalia and not extending to the groin. The lateral separation of the electrodes 30 in some embodiments may be less than the embodiments described above in relation to FIGS. 1 and 2. On the posterior side illustrated in FIG. 8B, electrodes 30 may be approximately placed over the dimples that are commonly visible at the top inside part of the buttocks, generally corresponding with a lower lumbar or sacral region overlying or adjacent parts of the sacrum or ilium. The lateral spacing of the posterior electrodes may thus be between about 1 cm and about 10 cm, for example. Optionally, the posterior electrodes 30 may be positioned slightly higher than the upper extent of the sacrum or ilium so as to reduce the likelihood of electrical current being directed through the bones of the sacrum and ilium as interferential current is passed between the anterior and posterior electrodes 30.

Figure 9:
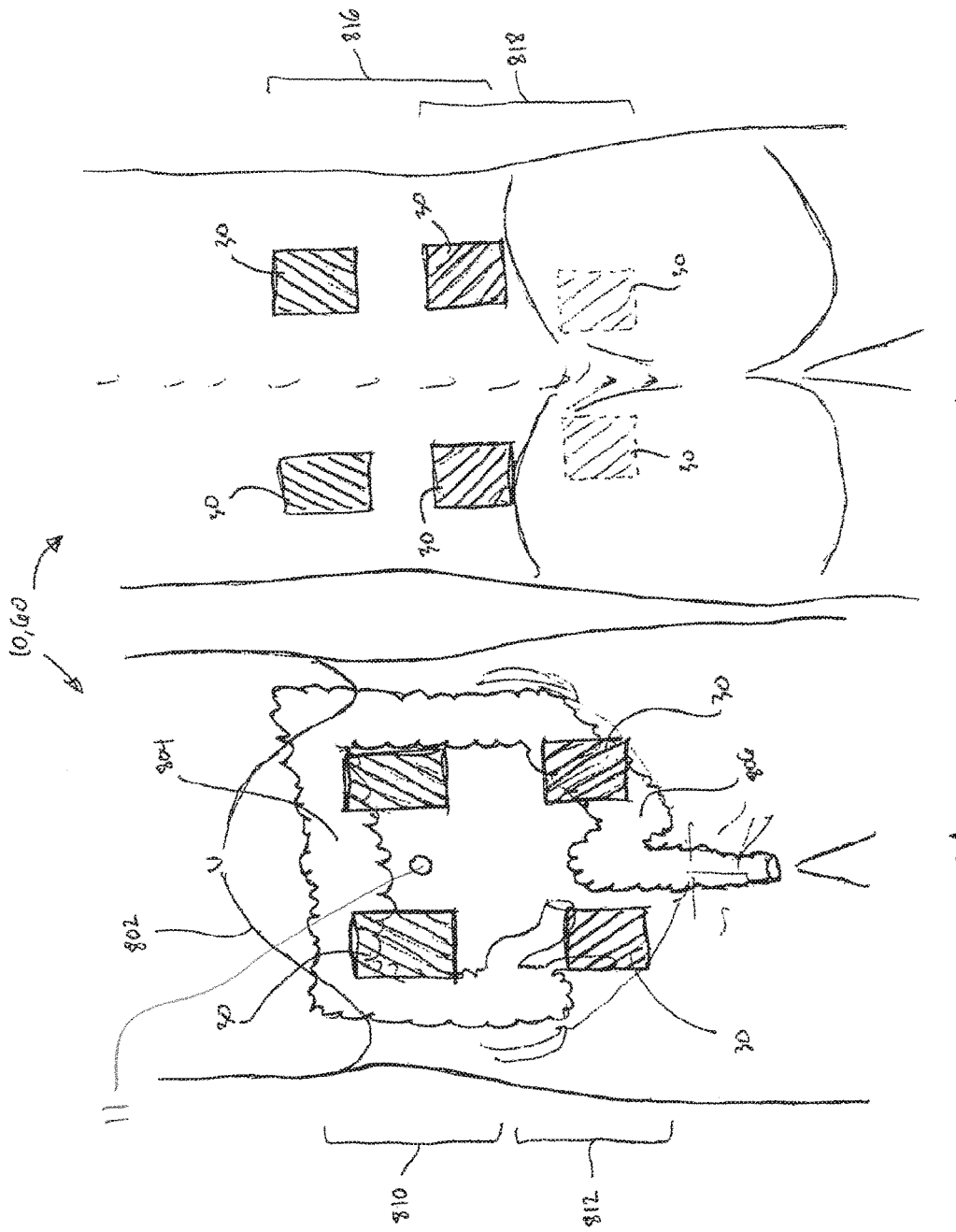
FIG. 9A is a schematic illustration showing placement of multiple frontal electrode pairs.
FIG. 9B is a schematic illustration showing placement of multiple posterior electrode pairs.

Some embodiments may employ more than two pairs of electrodes, such as the four pairs illustrated in FIGS. 9A and 9B. In such embodiments, the electrode positions illustrated in FIGS. 1, 2, 8A and 8B may be combined, with two electrode pairs 810, 812 laterally and vertically spaced in anterior abdominal (810) and lower pelvic (812) areas. Additionally, on the posterior side, two pairs of electrodes 816, 818 are laterally and vertically spaced relative to the spine. The lower pair of posterior electrodes (818) may be positioned just above the buttocks on either side of the spine or in a lower position that overlies an upper inner part of the buttocks overlying or adjacent the sacrum or ilium. The upper pair (816) of electrodes 30 may be positioned generally opposite the corresponding anterior upper pair (810) of electrodes 30 so as to be located in a para-spinal area on each lateral side of lumbar vertebrae T9-10 to L2.

In the embodiments as illustrated in FIGS. 9A and 9B, the electrodes 30 may be operated in two upper pairs and two lower pairs to deliver interferential current stimulation in sequence with one another or simultaneously. In some embodiments, the interferential current may be applied between opposed upper and lower electrodes. For example, stimulation current may be applied between one lower posterior electrode 30 and one diagonally opposite upper anterior electrode 30 and optionally also one diagonally opposite lower anterior electrode 30.

The upper electrode pairs should be located below the costal margin 802 and generally be positioned to excite or modulate parts of the ascending, transverse and descending colon 804, while the lower pairs of electrodes 30 should be generally positioned above the anus and genitals so as to excite or modulate the rectum and thereby assist in treatment of anorectal retention. The two upper and two lower pairs of stimulation electrodes 30 are believed to be likely to have a combined positive treatment effect for evacuation dysfunction affecting parts of the large bowel, including the proximal colon as well as parts of the large bowel distal of the proximal colon, such as the sigmoid colon 806 and rectum.

Figure 10:
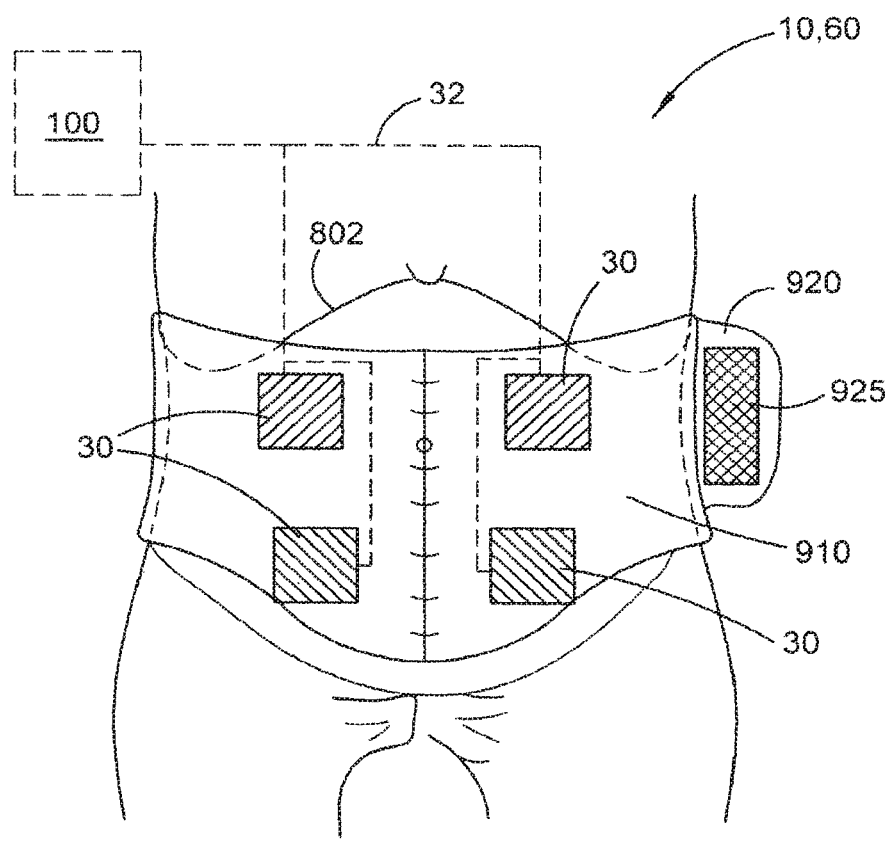
FIG. 10 is a schematic diagram of a belt for assisting electrode placement of single or multiple frontal and posterior electrode pairs.

Referring now to FIG. 10, a wearable electrode carrying structure in the exemplary form of a belt arrangement 910 is schematically illustrated. The belt 910 carries two pairs of anterior electrodes 30 and a further two pairs of posterior electrodes 30 (not shown) to provide TES using interferential current delivered from device 100 using conductors 32. Conductors 32 are at least partially supported by the belt 910 and are preferably threaded or passed through at least part of the belt 910 or portions thereof. Belt 910 may comprise carrying means, such as a pocket, pouch, cradle or attachment mechanism, to support and carry the device 100 as the patient moves around.

Although the belt 910 is illustrated as having electrodes 30 positioned to provide TES in the manner described in relation to FIGS. 9A and 9B, belt 910 may instead carry a single anterior pair (810/812) and a single posterior pair (816/818) of electrodes for placement in the regions as illustrated in FIGS. 1, 2, 8A and 8B.

In further embodiments, the belt 910 may comprise a selectable array of interior electrode connection positions by which the electrode 30 is fixed relative to the belt and is in electrical communication with conductors 32 in any of the array of positions. In this way, one or more than one pair of electrodes 30 may be provided anteriorly and one or more than one pair of electrodes 30 can be provided at a selected position or positions posteriorly according to the desired treatment regime prescribed by a medical professional. Once suitable positions of the electrodes 30 on the belt 910 are selected by the medical professional, the patient 10, 60 can simply place the electrodes 30 in the correct position on their skin for each treatment session by wearing the belt 910 in the same position with respect to the patient's own anatomy.

Belt 910 may be suitably flexible and may be fitted and removed by suitable coupling means, for example such as a side flap 920 having fastening means 925 thereon, such as hook and loop fasteners, buttons or clasps. Belt 910 may be formed of one or more individual or composite layers of flexible (optionally at least partially stretchable) fabric, including for example leather, Lycra, Spandex, cotton, nylon, plastic or other suitable fabric, to provide a wearable garment structure to support the device 100, conductors 32 and electrodes 30. Belt 910 may be generally fluid permeable or impermeable. Preferably, belt 910 is made of one or more machine-washable materials. Belt 910 is preferably sized to be worn with reasonable comfort underneath normal clothing so that a patient wearing the belt 910 can perambulate normally while undergoing the TES.

In self-administering the treatment prescribed by the medical professional, each patient may be instructed to follow particular instructions for care of the electrodes and their placement in order to maximise effective delivery of the TES.

Modifications of the described embodiments may be apparent to those skilled in the art, without departing from the spirit and scope of the described embodiments. The described embodiments are therefore intended to be exemplary and non-limiting when considered in the context of the appended claims.

Studies involving some described embodiments are described by the following non-limiting Examples.

EXAMPLE 1

Daily Transcutaneous Electrical Stimulation Increases Defecation in Children with Slow-Transit Constipation Patient Groups Halfway through a randomized control trial (Clark et al, 2009 supra) (RCT) testing transcutaneous electrical stimulation (TES), battery-operated machines became available, thus allowing home-based stimulation by parents. Eleven children (6M/5F, mean 14 yr, range 12-18 yrs) with slow-transit constipation who completed the RCT study, but relapsed or without an increase in defecation, were offered the opportunity to try the machine by a paediatrician (11±5 months after TES trial). These children all had chronic constipation and soiling for a minimum of two years prior to the RCT and had failed to respond significantly to the TES in the trial, as well as medical treatments such as dietary modifications, oral and rectal laxatives.

All eleven children had undergone a radio-nuclear transit study to show slow-transit in the transverse colon. However, one child was found to have normal colonic transit and because of that he was excluded from the TES Trial. He still had the TES treatment but did not have any improvement, so he was included in this study. Another child had more severe symptoms requiring an appendix stoma and his constipation and soiling was managed with antegrade washouts every 2-3 days (King et al, *J. Pediatr. Surg.*, 40:1935-1940, 2005).

Stimulation Regime Parents of the children were trained to use the battery-operated interferential stimulating machine (EPM IF 4160, Fuji Dynamics, Hong Kong) by the trial physiotherapist. Stimulation was performed and monitored by the parents at home (1 hour daily for a minimum of 2 months). Interferential treatments delivered a 4 kHz carrier frequency, a beat frequency of 80-150 Hz with an intensity of <33 mAmp. Two adhesive 3 $cm^2$ electrodes were placed on the anterior abdominal wall below the costal margin of the children and two other electrodes placed on the posterior abdominal wall between T9 and L2 on either side. The current from the electrodes was crossed diagonally from front to back to ensure that the stimulation current from each electrode crossed over within the abdomen of the child.

Outcome Measures The number of spontaneous and "sit" defecations, number of antegrade enema washouts or medication and number of incidents of soiling were recorded daily in a specially designed continence diary. The daily diary was kept one month prior and for two months during electrical stimulation. The (a) frequency of defecation, (b) frequency of soiling and (c) frequency of episodes of abdominal pain per month were compared using ANOVA with post-test analysis and paired t-tests (two tailed). P values<0.05 were considered statistically significant.

Results

Figure 7:
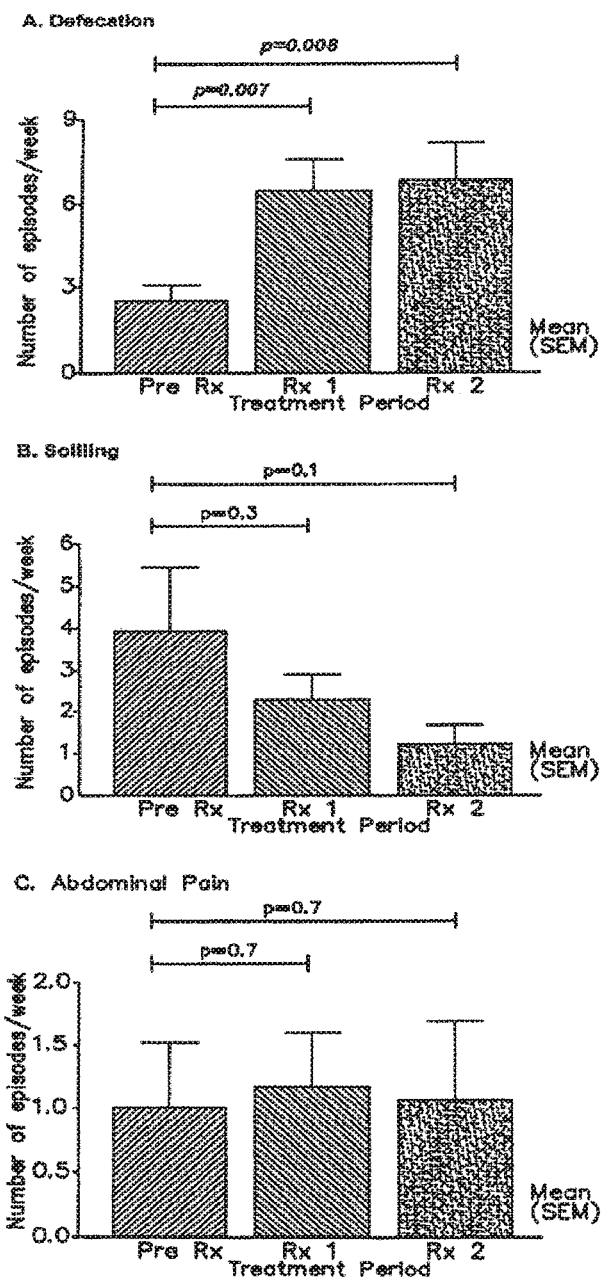
FIG. 7 is a graphical representation showing before and after daily stimulation treatment for 1 month (Rx1) and 2 months (Rx2) in 11 patients:
A) Total number of defecations/week,
B) Number of days with soiling, and
C) Number of days with abdominal pain.

FIG. 7 is a graphical representation showing:
A) Total number of defecations/week,
B) Number of days with soiling, and
C) Number of days with abdominal pain.

Daily diaries were assessed for 1 month before stimulation (Pre Rx), and during the first month (Rx 1) and second month (Rx 2) of stimulation performed daily at home. Statistically analysis by paired t-test.

There were no adverse events or complaints of discomfort reported from the children. All patients tolerated home stimulation well.

a) Defecation From Table 1, defecation increased in nine out of eleven children. There was a significant increase (p=0.008) in total defecation per week (mean±SD, 2.5±2.1 vs 6.7±4.4) (FIG. 7A). Five of the eleven patients had less than three defecations/week in the baseline period and all of them had normal episodes of defecation (>3/week) during stimulation. Six children had an increase in spontaneous defecation (Table 1) and three experienced increase in defecation during trained sits on the toilet. One child had no increase in total defecation but there was a marked increase in spontaneous defecation i.e. changes from timed sits to spontaneous defecation (urge to defecate followed by the child performing controlled defecation in the toilet).

b) Soiling There was a qualitative decrease in four out of eleven children, however this was not statistically significant (3.8±1.6 vs 1.1±0.5 episodes/week) (p=0.1) (FIG. 7B). In the baseline period, soiling was frequent in 3/11 children (Table 1). This was reduced to low episodes during stimulation in all of the three children. The patient with an appendix stoma had his soiling managed by antegrade enemas and therefore recorded no soiling.

c) Pain Daily stimulation did not affect abdominal pain (0.97±1.8 vs 1.03±2.0 episodes/week, p=0.7) (FIG. 7C).

This study found that the use of a battery-operated, portable machine was safe to deliver interferential TES in the home environment. Moreover, daily stimulation of one hour per session for >1 month caused a significant increase in total episodes of defecation/week, with no adverse effects. Importantly, this improvement in bowel function occurred in patients who had had only marginal or temporary improvement following stimulation three times per week in our recently conducted randomized controlled trial (Clark et al, *J. Pediatr. Surg.*, 43:320-324, 2008).

In the formal trial, the TES was given for 20 minutes in each treatment session, three times per week, so that the total duration of therapy was one hour per week. When the trial was designed, the optimal parameters (if any) were unknown, and hence were selected on arbitrary criteria. Having demonstrated a statistical improvement in transit times (Clark et al, 2009 supra), 24-hour colonic manometry (King et al, Am. J. Gastroenterol., 103:2083-2091, 2008), and quality of life (Clark et al, 2008 supra) in the trial, the current study aimed to find out whether more frequent TES treatment might further improve function.

Daily TES at home enabled the children in this pilot study to receive 7 hours of treatment per week (compared to 1 hour per week in the formal trial), which improved their overall bowel function in frequency of defecation. Interestingly, this was one of the few parameters which was not improved in the randomized placebo-controlled trial, despite increased colonic transit and peristaltic activity. The reason for this difference is unknown but it may be that TES three times per week caused increased proximal colonic transit, but without altering rectal evacuation. The children then needed to learn how to defecate normally to take advantage of this increased proximal colonic contractility. In this pilot study, improved defecation may have occurred because more time had passed since the trial and the patients were better able to learn how to empty their colon under conscious control. Another possibility is that the increased time length and frequency of treatment from 1 hour to 7 hours per week provided a much more substantial stimulus to colonic function, enabling not only more rapid proximal transit but also more effective evacuation.

There was concern that the electrical stimulation might increase soiling but this did not occur. Daily stimulation showed a qualitative reduction in frequency of soiling but this was not statistically significant. Although more patients need to be tested, it is considered that this qualitative improvement is likely to be important. The frequency of abdominal pains, assumed to be caused by colonic peristalsis, was also measured and this is unchanged by the daily TES.

TES has only been tested in very limited studies in children, outside the controlled trial described herein, so its place in the armamentarium of constipation therapies is unknown. The initial pilot study with TES used sophisticated machines connected to the power grid and operated by a licensed physiotherapist (Chase et al, J. Gastroenterol. Hepatol, 20:1054-1061, 2005). This study extends that and shows that a simpler machine with a 9-volt rechargeable battery is adequate to provide the requisite stimulation, and may even provide superior effects on the bowel.

The RCT showed that TES is significantly more effective than a placebo. Hence, an increased duration and frequency of TES treatment times is an advantage.

In the cohort of children being treated for slow transit constipation by transcutaneous electrical stimulation using the battery-operated interferential stimulating device (EPM IF 4160, Fuji Dynamics, Hong Kong), it was found during patient follow-up that there were some treatment efficacy problems arising from misuse or improper use of the device. The Fuji Dynamics device has a relatively large number of buttons to push and many stimulation settings and options to choose from.

In one case, the parent was confused by which buttons to push to get the proper settings for the treatment (needing 6 buttons to be pushed). This parent was also illiterate and the written instructions for use were essentially useless, leading to a hands-on demonstration of use of the device being needed in order to make sure the parent was getting the stimulation settings right. It was also found that the patient or the parent would commonly forget to set the buttons to achieve the essential settings for treatment. In one instance, a patient had gone through the treatment period without setting the stimulation frequency, resulting in inadequate stimulation being applied and the patient not experiencing any improvement in symptoms.

In younger children, it has been found that they tend to play with the buttons of the device. The Fuji Dynamics device used in the trial did not have any locking features to prevent inappropriate user modification of the device settings. One child experienced shooting pain in both legs after changing the stimulation settings on the device.

EXAMPLE 2

TES Treatment Long Term Benefits

In a follow-up study of patients that have previously been enrolled in a TES trial it was noted that there was continued improvement in patients after the time of usage of TES.

There are total of 105 patients which have been included into the transcutaneous electrical stimulation (interferential) therapy (Table 2). They comprise of 66 male patients and 39 female patients. The age ranges of these patients are 6 -18years, with the mean age of 11.5 years. All these patients have been selected for the treatment after being diagnosed with slow transit constipation using nuclear transit study. There are different phases of development of the transcutaneous electrical stimulation, from TIC TOC to TENS trial and the home stimulation therapy. All patients were required to fill out the continence diaries and PedsQL questionnaires appropriate to age upon enrolment into the trial and as the scheme for follow-up during and after treatment.

In the TIC TOC trial, at 6 months follow-up, out of the 39 patients with data analysed at the completion of the trial, 20 patients responded to the questionnaires survey. Sixteen out of 20 patients have >3 episodes of defecations per week at 6 months after treatment. At 12 months follow-up, 13 responded to the questionnaire survey. Eleven out of 13 patients have >3 episodes of defecations per week. As for soiling, at 6 months follow-up, 14 out of 23 respondents have no soiling. At 12 months follow-up, 6 out of 11 respondents have no soiling. There was overall improvement in patients with slow-transit constipation treated by transcutaneous interferential therapy.

In the latest home stimulation therapy, one patient has complete resolution of abdominal pain, twofold increase in defecation, and 3.7-fold improvement of soiling at one month follow-up.

The described stimulation regimes in Examples 1, 2 and 3 have been used without also directly stimulating the pelvic floor or area around the perineum or perianum.

EXAMPLE 3

There are 4 children currently using the Anorectal retention (AR) protocol to treat their chronic constipation, the results of which are shown in Table 3. The position of the electrodes 30 is shown and described above in relation to FIGS. 8A to 8C. The stipulated TES treatment regime and settings were the same as the other Examples, including the treatments being for about 60 minutes each day over a period of several weeks or months.

TABLE 3

Children with chronic constipation using AR protocol.

| | Gender | Age | Clinical diagnosis of chronic constipation | Elecrode positions used | Current status (25 Feb 2011) |
|---|---|---|---|---|---|
| 1 | Male | 9 | Slow-transit constipation (STC) | STC protocol, developed AR (palpable faecaloma) 6 months later. AR protocol used. | Clinically improved after 6 months and remained well (phone interview done 22 Feb 2011). No more faecaloma. |
| 2 | Male | 4 | STC | STC protocol for 6 months. Repeat transit study showed AR. Started AR protocol December 2010. | Feeling stronger urge at bottom with reduced laxative used (phone interview done on 22 Feb 2011) |
| 3 | Male | 6 | STC + Anorectal retention (AR) | Used STC protocol for 4 months before switched over to AR protocol. | Clinically improved with more regular bowel actions. Remained same (phone interview done on 22 Feb 2011). |
| 4 | Female | 6 | AR | Palpable faecaloma. Started on AR protocol on 17 Sep 2010. | Still awaiting phone reply from parent. |

As these preliminary data in Table 3 indicate, TES treatment using interferential current applied at lower pelvic and sacral regions is effective to treat evacuation dysfunction in the recto-sigmoid colon. This has been shown to be effective as a procedure performed after treatment at higher electrode positions for STC. The indication is that this lower electrode positioning can be used as a supplemental or independent procedure to the higher electrode positioning. If the treatment procedure with the lower electrodes is supplemental to the treatment with higher electrodes, it may be performed either simultaneously or in sequence.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 1

| Sex | Appendix Stoma | Transit Study | Defecation/week | | | | Days with soiling/week | | | Days with pain/week | | |
|---|---|---|---|---|---|---|---|---|---|---|---|---|
| | | | Before | IFT 1 | IFT 2 | Change | Before | IFT 1 | IFT 2 | Before | IFT 1 | IFT 2 |
| With slow transit and no appendix stoma | | | | | | | | | | | | |
| F | No | Slow | 0 | 12 | 14 | ½ sits & spontaneous | 0 | 3 | 0 | 0 | 1 | 0 |
| F | No | Slow | 0 | 4 | ND | ↑ sits | 0 | 1 | ND | 3 | 0 | ND |
| F | No | Slow | 1 | 3 | ND | ↑ spontaneous | 6 | 1 | ND | 5 | 5 | ND |
| F | No | Slow | 3 | 11 | 11 | ↑ sits | 7 | 3 | 3 | 0 | 1 | 1 |
| F | No | Slow | 7 | 10 | 12 | ↑ spontaneous | 2 | 0 | 0 | 0 | 2 | 0 |
| M | No | Slow | 1 | 4 | 3 | ↑ spontaneous | 0 | 0 | 0 | 1 | 3 | 4 |
| M | No | Slow | 2 | 6 | 6 | ↑ spontaneous | 3 | 5 | 3 | 0 | 1 | 1 |
| M | No | Slow | 3 | 2 | 4 | ↑ spontaneous | 0 | 0 | 0 | 0 | 0 | 0 |
| M | No | Slow | 4 | 2 | 3 | ½ sits & spontaneous | 4 | 4 | 3 | 0 | 2 | 1 |
| With appendix stoma | | | | | | | | | | | | |
| M | Yes | Slow | 3 | 5 | 9 | ↑ spontaneous | 0 | 0 | 0 | 0 | 0 | 0 |
| With Normal Transit | | | | | | | | | | | | |
| M | No | Normal | 4 | 12 | ND | ↑ sits | 7 | 2 | ND | 2 | 0 | ND |

ND: No Data

TABLE 2

TIC TOC
Started with 60 patients; 39 patients available for analysis
and on follow-up. Follow-up periods of 1 year to 2 years.
21 patients were excluded from study.

| GENDER | NUMBER (N) |
|---|---|
| MALE | 21 |
| FEMALE | 18 |

AGE RANGES FROM 7-18 YEARS, MEAN AGE OF 11.8 YEARS (OF THE 39 PATIENTS INCLUDED IN THE FINAL ANALYSIS).

| GENDER | NUMBER (N) |
|---|---|
| MALE | 39 |
| FEMALE | 21 |

AGE RANGES FROM 6-18 YEARS, MEAN AGE OF 12.3 YEARS (OF THE 60 PATIENTS AT THE BEGINNING OF THE STUDY)

TENS

| GENDER | NUMBER (N) |
|---|---|
| MALE | 5 |
| FEMALE | 5 |

AGE RANGES FROM 5-16 YEARS, MEAN AGE OF 9.3 YEARS. FOLLOW-UP OF PATIENTS FROM 6 MONTHS TO 1 YEAR $1^{ST}$ HOME STIMULATION THERAPY

| GENDER | NUMBER (N) |
|---|---|
| MALE | 6 |
| FEMALE | 5 |

AGE RANGES FROM 9-15 YEARS, MEAN AGE OF 12 YEARS. FOLLOW-UP OF PATIENTS FROM 6 MONTHS TO 1 YEAR.

$2^{ND}$ HOME STIMULATION THERAPY

| GENDER | NUMBER (N) |
|---|---|
| MALE | 16 |
| FEMALE | 8 |

AGE RANGES FROM 4-16 YEARS. MEAN AGE OF 10.3 YEARS FOLLOW UP OF PATIENTS FROM 0-5 MONTHS.

BIBLIOGRAPHY

Benninga et al, *J Pediatr Gastroenterol Nutr.*, 23:241-51, 1996

Chase et al, *J. Gastroenterol. Hepatol.*, 20:1054-1061, 2005

Clark et al, *J. Pediatr. Surg.*, 43:320-324, 2008

Clark et al, *J. Pediatr. Surg.*, 44:408-412, 2009

Hutson et al, *J Pediatr Surg.*, 31:580-583, 1996

King et al, *J. Pediatr. Surg.*, 40:1935-1940, 2005

King et al, *Am. J. Gastroenterol.*, 103:2083-2091, 2008

Shin et al, *J Pediatr Surg.*, 37:1762-1765, 2002

What is claimed is:

1. A system for transcutaneously treating a waste evacuation dysfunction, comprising:
at least four electrodes comprising a first pair of electrodes positioned one on each lateral side of the spine or sacrum in the sacral region and a second pair of electrodes positioned laterally across the lower pelvic region; and
a stimulation device configured to provide electrical stimulation signals to the at least four electrodes to perform a technique for treating a waste evacuation dysfunction, wherein while performing the technique, the stimulation device is configured to administer transcutaneous electrical stimulation (TES) to at least one lower pelvic region and at least one sacral region for at least one treatment period per day over a treatment term of at least one week, wherein the TES comprises interferential electrical stimulation.

2. The system of claim 1, wherein the stimulation device is configured to have a single set of stored stimulation settings that control the provision of the electrical stimulation signals.

3. The system of claim 2, wherein the stimulation device is free of user-operable controls that would allow modification of the stimulation settings.

4. The system of claim 2, wherein the stimulation device comprises a port coupleable to an external computing device to allow modification of the stimulation settings.

5. The system of claim 1, wherein the stimulation device stores a limited set of selectable stimulation settings that control the provision of the electrical stimulation signals.

6. The system of claim 1, wherein the at least four electrodes comprise a first pair of electrodes positioned one on each side of the umbilicus and a second pair of electrodes positioned in a para-spinal area on each side of lumbar vertebrae T9-10 to L2.

7. The system of claim 1, wherein the at least one electrode is carried on a carrier substrate adhered to the skin by a manually releasable adhesive.

8. The system of claim 7, wherein the carrier substrate carries at least two electrodes spaced a substantially fixed distance apart across the substrate.

9. The system of claim 1, further comprising a wearable structure to carry the stimulation device and to assist in positioning the at least one electrode on the skin.

10. The system of claim 9, wherein conductors electrically coupling the stimulation device to the at least one electrode are supported by the wearable structure.

11. The system of claim 10, wherein the conductors at least partially pass through the wearable structure.

12. The system of claim 9, wherein the wearable structure comprises a belt.

13. The system of claim 11, wherein the stimulation device comprises at least one accelerometer to detect at least one of movement and orientation of the stimulation device.

14. The system of claim 11, wherein the stimulation device comprises means to assess patient compliance with the treatment regime based on information collected and stored on the stimulation device regarding patient usage of the stimulation device.

15. The system of claim 11, wherein the stimulation device comprises a microcontroller having a timing function and configured to disallow further administration of electrical stimulation for a period following provision of electrical stimulation.

16. The system of claim 1, wherein the system is using to treat at least one of: constipation; slow transit constipation; ileus; incontinence; and anorectal retention.

17. A system for treating constipation, comprising:
a first and second plurality of electrodes; and
a stimulation device operably connected to the first and second plurality of electrodes, wherein the stimulation device is configured to:
administer, using the first plurality of electrodes, a first transcutaneous electrical stimulation (TES) between at least one lower pelvic region and at least one sacral region of a patient;
administer, using the second plurality of electrodes, a second TES between at least one abdominal region and at least one lumbar region of the patient; and administer the first and second TES for at least one treatment period per day over a treatment term of at least one week for constipation treatment, wherein the first and second TES each comprises interferential electrical stimulation.

18. The system of claim 17, wherein the first plurality of electrodes comprises a first pair of electrodes configured to be positioned one on each side of an umbilicus of the patient and the second plurality of electrodes comprises a second pair of electrodes configured to be positioned in a paraspinal area on each side of lumbar vertebrae T9-10 to L2 of the patient.

19. The system of claim 17, further comprising a wearable belt, the belt configured to support the stimulation device and the first and second plurality of electrodes such that each electrode is in the correct position on the patient for administering the first and second TES.

20. The system of claim 17, wherein the first plurality of electrodes comprises a first and second pair of electrodes, and the second plurality of electrodes comprises a third and fourth pair of electrodes.

* * * * *